US005576026A

United States Patent [19]
Charter et al.

[11] Patent Number: 5,576,026
[45] Date of Patent: Nov. 19, 1996

[54] LUMBRICUS PRODUCT AND METHOD OF MAKING SAME

[76] Inventors: Edward A. Charter, 2354 Anora Dr., Abbotsford, British Columbia, Canada, V2S 5P8; Seung H. Lee, 31212 Peardonville Rd., Abbotsford, British Columbia, Canada, V25 5W6

[21] Appl. No.: 316,110

[22] Filed: Sep. 30, 1994

[51] Int. Cl.$^6$ .............................. C12P 21/06; A61K 35/12
[52] U.S. Cl. .................... 424/520; 435/68.1; 435/212; 435/219; 435/226
[58] Field of Search ..................... 424/520; 435/68.1, 435/212, 219, 226

[56] References Cited

U.S. PATENT DOCUMENTS 4,568,545  2/1986  Mihara et al. ....................... 424/94.64
5,128,148  7/1992  Ishii et al. ................................ 424/520

OTHER PUBLICATIONS

Biotech Abs. 93–11416 Abstract SU1752759 (Aug. 1992).

Primary Examiner—Herbert J. Lilling
Attorney, Agent, or Firm—Robert B. Hughes

[57] ABSTRACT

A method of making a lumbricus powder wherein there is provided a quantity of worms which are cleaned and then masticated. The masticated worms are then hydrolyzed, this being accomplished by immersing the masticated worms in an enzyme ingredient. Then the product is freeze dried to make a lumbricus powder.

6 Claims, No Drawings

LUMBRICUS PRODUCT AND METHOD OF MAKING SAME

The present invention relates to a method of making a lumbricus product and also to the product itself, and more specifically a method of making a lumbricus product having natural pharmaceutical and/or medicinal properties and also to such a product.

BACKGROUND OF THE INVENTION

The earth worm identified as "*Lumbricus rubellus*" and other species has a dictionary definition (Merrian Webster's Collegiate Dictionary—Tenth Edition) of being a terrestrial annelid worm (Class Oligochaeta); any of family (Lumbricuidae) of numerous widely distributed hermaphroditic worms that move through the soil by means of setae. In North America, these have been popular for use as fishing bait, and more recently they are becoming an important component in composting operations, primarily for their ability to break down large amounts of organic matter. These are raised on a large scale in worm farms.

In oriental countries, worms have long been used as a medicine. The Oriental Herb Index, written by Joon Huh in Korea mentions the use of worms to treat fever, seasonal epidermic infections and sore throats amongst other illnesses. The Basic Herb Index, written by Si Jin Lee in China mentions treatment of infantile fever, paralysis, sore throat and nephritis (a condition in which there is a loss of Na+ ions in the urine that requires a high salt intake to prevent cardio vascular collapse).

Historically, these worms have been processed in oriental countries in various ways, and examples of this are the following:

a. collecting adult worms in March and drying them in the sun to be used in making worm powder;

b. collecting and washing the worms in water, then adding salt to make a liquid worm slurry;

c. collecting the worms and burning them in a fire which results in an ash for making powder.

The worms which are included within the strict definition of "*Lumbricus rubellus*", are somewhat rare. Accordingly, as a practical matter, other worms are often used in the place of the *Lumbricus rubellus* for the uses noted above. For example, when these worms are used to make a powder having pharmaceutical or medicinal properties, this powder is commonly referred to as "Lumbricus powder", even though this is made of worms that are not within the strict definition of *Lumbricus rubellus*. Examples of other worms which are used to make Lumbricus powder are the following: *Eisenia foetida* and *Eisenia rosea*. Such worms are commonly grown in worm farms in the United States, South Korea and Japan.

Lumbricus powder has been made for a number of years by first causing the worms to discharge the earth and other materials in their digestive cavities, and then washing the same. The worms are then cut or otherwise formed into small particles (e.g. into a slurry); then these are formed into a powder in some manner.

SUMMARY OF THE INVENTION

It is an object to form a Lumbricus product (and more specifically a Lumbricus powder) having a desirable balance of advantageous characteristics, such as providing an end product which is made with ingredients or additives that are naturally occurring, has minimum bacterial content and also has a desirable appearance (preferably light brown color). Also, it is an object to provide such a product which has a desirable balance of characteristics to improve a person's health, and also to provide the process of making the product so that the healthful characteristics and other desirable characteristics are not degraded or destroyed in the processing.

In the method of the present invention, there is first provided a quantity of lumbricus worms and these are cleaned. The worms are then masticated. The masticated worms are then hydrolzed and dried to form the end product.

In the preferred embodiment, the hydrolyzing accomplished by adding an enzyme ingredient to the masticated worms this enzyme ingredient is desirably selected from a group of proteases and pancreatin.

Also, acid can be added to the masticated worms while hydrolizing. Further, lysozyme can be added to the masticated worms as these are being hydrolzed. The preferred method of drying the worms is by freeze drying.

Also, the preferred method of cleaning the worms is to immerse live worms in a salt water composition. More particularly, the worms are immersed in a salt water solution between about 0.95 to 0.9 percent sodium chloride and/or postassium chloride. The product with the present invention is made in accordance with the method described above.

DESCRIPTION OF THE PREFERRED EMBODIMENTS

A preferred embodiment of the present invention disclosed herein is a process for making Lumbricus powder which is adapted for human consumption to provide medicinal or other healthful benefits. The steps in the process of the present invention will be described under appropriate headings.

a. The Starting Material

The starting material are live worms such as those described earlier herein under "Background of the Invention". The term "Lumbricus" is (in the description of the present invention) intended not to refer simply to Lumbricus worms (*Lumbricus rubellus*), but also other worms having like characteristics which are used in the manufacture of what is commonly referred to as "Lumbricus powder". Thus, the designation of the end product, namely "Lumbricus powder" is intended to mean powder that is made from this broader category of live worms. As indicated above, such worms are grown in worm farms in the United States, North Korea and Japan.

b. Causing Discharge of Earth and Other Material From the Digestive Cavities of the Worms In the present invention this is accomplished by immersing the worms, while alive, in salt water having a concentration between 0.65 to 0.90 percent sodium chloride (NaCl) or potassium chloride (KCl). The temperature of the salt water is maintained between 15° and 25° C., and the immersion time is about 20 to 24 hours. These conditions are suitable for the worms to remain alive and discharge the soil and other material in a natural way.

Within the broader scope of the present invention it would be possible to cause the discharge of the earth and other material from the digestive cavities of the worms by simply immersing the worms in plain water. However, the preferred form is the immersion in the weak salt solution.

The worms can be immersed in one salt solution and then moved into another salt solution, and then possibly to a third. Alternatively, the worms could be immersed in a salt solution where the salt water is recirculated and purified to carry away some of the digestive matter discharged from the worms.

c. Washing the Worms

After the earth and other material has been discharged from the worms, the next step is to wash the worms. The preferred method of washing the worms is simply to pass clean water through (or over) the worms which at this point are still alive. This removes the salt and other residual material.

d. Mastication of the Worms

This mastication of the worms can be accomplished after cleaning while the worms are still alive. As an alternative, this mastication could take place by using previously cleaned worms that have been frozen into solid blocks (and thus killed), with the frozen worms then being thawed out and masticated. As a further alternative prior to the mastication, the worms can be contained in water that is at a sufficiently high temperature (e.g. 100° F. for a sufficient time) to first kill the worms. One possible benefit of this is that it may cause denaturation of the worm's skin. Thus, the heat treated worms could be more readily masticated or homogenized, thus possibly alleviating the need for specialized equipment. Conventional methods can be used to masticate the worms (break these up into small particles so as to form a "slurry". For example, the worms can be forced through a three millimeter screen, which would result in a homogenous slurry.

e. Hydrolyzing the Masticated Worms

The worms that are masticated already have sufficient water content (80 to 85%) so that the slurry resulting from the mastication is already sufficiently liquid. Accordingly, additional water is generally not required. The additives which are added to the slurry can be in powdered form. Alternatively, a small amount of water may first be added to the powdered additive simply to dissolve it. (This added water would generally be less than one percent of the total amount of water in the slurry).

One group of additives which can be used to accomplish the hydrolyzing are proteases, which are enzymes which break down other proteins. One type of protease which can be used is papain in an amount of equal to 0.1 to 0.5% of the total solids present depending on the enzyme activity level.

Also hydrolyzing can be accomplished by using pancreatin. Pancreatin is a mixture of enzymes that are separated from the pancreas of mammals, such as pigs or cattle. With regard to concentrations, the pancreatin should be added in the amount of 0.1 to 2 percent of solids in the worm slurry. This percentage is based upon the following. It is assumed that the pancreatin has an activity level of 1 USP. Therefore if the USP activity goes up, the amount of the pancreatin required would go down.

There are three basic types of enzyme activity that are specified by U.S. Pharmacopeia to be in 1×USP pancreatin. One type is protease activity, present at a minimum level of 25 USP protease units. A second is lipase activity (lipase is an enzyme that breaks down lipids), and this should be present at a minimum of 2 USP lipase units. The third, amylase activity, (amylase is an enzyme that breaks down starch), must be present at a minimum of 25 USP amylase units.

In addition to the enzyme or mixture of enzymes that is being added to carry out the hydrolysis, citric acid is added to the slurry, in the amount of one percent of the total worm solids. This citric acid is added primarily to accomplish chelation of iron ions in order to inhibit oxidation of the iron which may cause a dark color in the product. Another advantage of adding citric acid is tying up not only the iron ions but other metal ions that may be present in the solution. This may inhibit bacterial growth by removing access to the metal ions by the micro-organisms.

In addition to adding citric acid to the slurry while hydrolyzing, lysozyme is also added, this being a natural enzyme that occurs in tears, saliva and the white of an egg. This has an antimicrobial effect in that it breaks down the cell wall of certain types of bacteria. The lysozyme is added in the amount of about one percent for each one hundred parts of solid worm material by weight.

The main action of these ingredients is an anti-microbial action to effectively kill certain types of bacteria in the mixture. It is surmised that the combination of these three ingredients, namely the protolytic agent, (i.e. the pancreatin or papain), the citric acid and the lysozyme may have a synergistic effect in that they may work in combination better than each would work on its own. This is evidenced in some experiments that were carried out in which the bacterial levels dropped during the hydrolysis stage when these were added together. Also, it is believed that while adding the lysozyme and the citric acid enhances the process, within the broader scope of the present invention, it is still possible to generate a desirable product without these two powders. In certain situations, it may even be desirable not to use the lysosyme or citric acid.

The slurry with the hydrolyzing solution is maintained at a temperature of about 30° to 60° C. for a time period of between two to seven hours, with a preferred temperature range believed to be between 30° to 35° C.

f. Pasteurization

The pasteurization can be accomplished in a conventional manner. One method would be to simply place the slurry, after hydrolyzing, in a container which is jacketed, and water of the desired temperature is passed through the jacket area so as to precisely control the temperature. Another means would be to move the slurry through heat exchange passageways, possibly a scraped surface heat exchanger, and this may accomplish the heat transfer in a relatively shorter time because of the greater surface areas.

g. Drying

The preferred form of drying the slurry, after pasteurizing, is freeze drying. This can be accomplished by exposing the slurry to a vacuum environment at, for example, −40° to 40° C. The vacuum would normally be maintained below about 200 milli-torr. The freeze drying process will be continued until the composition is down to about 12% moisture content, at which time the remaining material is essentially a powder. Other forms of drying, such as spray drying could also be used. Pan drying did not prove to be effective.

After drying, the powder can desirably be ground so that the resulting powder has a more homogeneous particle size.

EXAMPLE 1

Frozen Lumbricus was obtained from a commercial source. A portion of this Lumbricus was thawed and allowed to sit at 4° C. for several days to permit an increase in the microbial population present. This was done to amplify the effect of pasteurization in this experiment. 500 milliliters of Lumbricus was masticated in a blender. Then exactly 500 milliliters (mL) was transferred into a 500 mL beaker. A sample was taken for microbiology testing, standard plate count (SPC) and coliform. The lumbricus was thereafter heated to 30° C. in a water bath. One gram of citric acid, one gram of granulated lysozyme powder, and one gram of 1×USP pancreatin was added to the lumbricus. It was then held at a temperature of 30° C. for 3 hours. After 3 hours, another sample was taken for microbial testing. To carry out the pasteurization, the sample was heated to 70° C. and held at this temperature for 15 minutes. The sample was then cooled to room temperature. Another sample was taken for microbial testing. Finally, the sample was poured into sterile stainless steel trays and lyophilized. A light brown powder was obtained. The microbial analysis results are presented in Table 1, along with the protein, ash and moisture content on a percentage basis for the finished powder.

TABLE 1

Microbiology testing results for EXAMPLE 1.

| Samples | SPC (cfu/g) | Coliform (cfu/g) | Protein |
|---|---|---|---|
| Moisture Ash | | | |
| Before hydrolysis | >9,350,000 | 45000 | |
| Before pasteurization | 2,230,000 | 370000 | |
| After pasteurization 13.4% 3.8% | 410,000 | 10 | 51.1% |

EXAMPLE 2

To study the effect of pasteurization time on the quality of lumbricus, about 1500 mL of frozen lubricus was thawed and held at 4° C. for about 2 weeks.

It was then homogenized in a blender. A sample was taken for microbial tests including standard plate count (SPC) and coliform. The Lumbricus was transferred into six 300 Ml beakers with 250 mL of sample in each beaker.

The beakers were heated to 30° C. in a stirring waterbath. 0.25 g of granulated lysozyme powder, 0.25 g of citric acid and 0.25 g of 1×USP pancreatin was added to each beaker.

The temperature of the samples was maintained at 39° C. for 3 hours. The samples were stirred constantly. Afterwards, a sample was taken from each beaker for microbial tests (SPC and coliform). The beakers were then heated to 70° C. The samples were then taken out in 5 minute intervals (5, 10, 15, 20, 25 and 30 minutes). All the samples were cooled to room temperature and microbial tests were then carried out. Finally, the samples were poured into sterile stainless trays and lyophilized.

A light brown product was obtained. The laboratory analysis results are summarized in Table 2.

TABLE 2

Microbiology testing results for Example 2.

| Samples | SPC (cfu/g) | Coliform (cfu/g) | Protein |
|---|---|---|---|
| Moisture Ash | | | |
| Before hydrolysis | >60,000,000 | 10100 | |
| After hydrolysis | 51,030,000 | 600 | |
| After 5 min. at 70° C. | 480000 | <10 | |
| After 10 min. at 70° C. | 440000 | <10 | |
| After 15 min. at 70° C. | 320000 | <10 | Average for all samples: 47.5% 13.3% |
| After 20 min. at 70° C. | 310000 | <10 | |
| After 25 min. at 70° C. | 290000 | <10 | |
| After 30 Min. at 70° C. | 300000 | <10 | |

EXAMPLE 3

One kilogram of live red worms (*Lumbricus rubellus*) were immersed in a solution of two liters of salt water (0.9% NaCl by weight) at 15° C. for ten hours to cause the discharge of undigested material from their inner cavity. After this, the worms were washed three times with the same amount of a weak salt solution (water with 0.9% NaCL) followed by a water wash to remove excess salt. The worms were then removed from the solution using a coarse screen and then pumped through a cutter having a fine screen (3 millimeter mesh). This produced a very viscous solution of the particles of worms.

The solution was then hydrolyzed by adding 0.02% papain at 55° C. for three hours, followed by pasteurization at 60° C. for three minutes.

The solution was then cooled at ambient temperature. The solution was then freeze dried, maintaining the freeze dry shelf temperature of below 48° C. for 48 hours. The vacuum was maintained below 100 m Torr to minimize the drying time. After the freeze drying, a yield of 150 grams of Lumbricus powder was obtained with a moisture content 10.5%, ash of 4.5%, and nitrogen content of 10.5%.

EXAMPLE 4

One kilogram of red worms "*Lumbricus rubellus*" was immersed in two liters of 0.7% NaCl solution at 12° C. for twelve hours to cause the undigested materials to be discharged from the worms. After complete discharge from the cavities of the worms, the worms were washed three times with the same amount of a salt water solution (0.7% NaCl). The worms were then removed from the solution using the coarse screen, and then pulped through a cutter with a fine mesh screen (3 millimeters). This resulted in a very viscous solution of worm particles. The solution was then hydrolyzed by adding 0.02 papain at 45° C. for three hours and then cooling the solution to ambient temperature. Following hydrolysis, the worms were heated at 65° for one minute. The solution was then freeze dried, maintaining the freeze dry shelf temperature below 55° C. for seventy two hours. The vacuum was maintained below 100 m Torr to minimize the drying time. A yield of 146 grams of Lumbricus powder was obtained with a moisture content of 11.2%, ash of 4.9% and nitrogen content of 10.6%.

EXAMPLE 5

One kilogram of red worms (*Lumbricus rubellus*) were immersed in two liters of 0.9% NaCL solution at 15° C. for ten hours to cause the discharge of undigested material from their inner cavities. After complete discharge, the worms were washed two times in the same amount (0.9% NaCL)

solution followed by a water wash. The worms were then removed from the solution by using a coarse screen, and then pulped using a cutter fitted with a fine mesh screen (3 mm). This resulted in a very viscous solution of worm particles. The solution was then hydrolyzed by adding 0.01 pancreatin (1× USP) at 40° C. for three hours, then cooled to ambient temperature. Following hydrolysis, the worms were heated at 62° C. three minutes. The solution was then freeze dried, maintaining the freeze dryer shelf temperature below 55° C. for ninety six hours. The vacuum was maintained below 100 m Torr to minimize the drying time. A yield of 152 grams of Lumbricus powder was obtained with a moisture content of 10.7% ash of 4.6% and nitrogen content of 10.2%.

What is claimed:

1. A method preparing a lumbricus product, comprising:
   a. providing a quantity of lumbricus worms and cleaning said worms;
   b. masticating the worms;
   c. hydrolyzing the masticated worms, said hydrolyzing being accomplished by adding an enzyme ingredient to said masticated worms, with said enzyme ingredient being selected from a group consisting of proteases, pancreatin and combinations thereof;
   d. adding an acid and lysozyme to said masticated worms while hydrolyzing is accomplished;
   e. drying the hydrolyzed masticated worms to form the lumbricus product.

2. A method preparing a lumbricus product, comprising:
   a. providing a quantity of lumbricus worms and cleaning said worms;
   b. masticating the worms;
   c. hydrolyzing the masticated worms said hydrolyzing being accomplished by adding an enzyme ingredient to said masticated worms, with said enzyme ingredient being selected from a group consisting of proteases, pancreatin and combinations thereof;
   d. adding lysozyme to said masticated worms while said masticated worms are being hydrolyzed;
   e. drying the hydrolyzed masticated worms to form the lumbricus product.

3. The method as recited in claim 1, wherein said drying is accomplished by freeze drying.

4. The method as recited in claim 2, wherein said drying is accomplished by freeze drying.

5. The method as recited in claim 2, wherein said cleaning is accomplished by immersing live worms in a salt water composition.

6. The method as recited in claim 5, wherein said cleaning is accomplished by immersing said worms in a salt water solution between about 0.65 to 0.9 percent sodium chloride and/or potassium chloride.

* * * * *